(12) United States Patent
Weismantel et al.

(10) Patent No.: US 8,119,755 B2
(45) Date of Patent: Feb. 21, 2012

(54) PROCESS FOR PRODUCING WATER-ABSORBING POLYMER PARTICLES

(75) Inventors: Matthias Weismantel, Jossgrund-Oberndorf (DE); Rüdiger Funk, Niedernhausen (DE); Leigh R. Blair, Greenwood Springs, MS (US); Kevin D. Heitzhaus, Suffolk, VA (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/498,153

(22) Filed: Jul. 6, 2009

(65) Prior Publication Data

US 2010/0010184 A1 Jan. 14, 2010

Related U.S. Application Data

(60) Provisional application No. 61/079,991, filed on Jul. 11, 2008.

(51) Int. Cl.
*C08F 20/06* (2006.01)
(52) U.S. Cl. ............. 526/317.1; 526/922; 526/930
(58) Field of Classification Search ............. 422/200; 526/317.1
See application file for complete search history.

(56) References Cited

U.S. PATENT DOCUMENTS

| | | | |
|---|---|---|---|
| 3,643,733 A * | 2/1972 | Hall et al. ............ | 165/81 |
| 2004/0234607 A1 | 11/2004 | Irie et al. | |
| 2008/0194863 A1* | 8/2008 | Weismantel et al. ...... | 562/400 |
| 2008/0214749 A1* | 9/2008 | Weismantel et al. ...... | 526/73 |
| 2008/0242816 A1 | 10/2008 | Weismantel et al. | |
| 2009/0221746 A1 | 9/2009 | de Marco et al. | |

FOREIGN PATENT DOCUMENTS

| | | |
|---|---|---|
| EP | 0 372 706 A2 | 6/1990 |
| EP | 0 574 260 A1 | 12/1993 |
| EP | 1 470 905 A1 | 10/2004 |
| WO | WO-03/051415 A1 | 6/2003 |
| WO | WO 2006/100300 A1 * | 9/2006 |
| WO | WO 2006100300 A1 * | 9/2006 |
| WO | WO-2007/028746 A1 | 3/2007 |
| WO | WO-2007/028747 A1 | 3/2007 |
| WO | WO 2007/028751 A2 * | 3/2007 |
| WO | WO-2007/028751 A2 | 3/2007 |
| WO | WO 2007028751 A2 * | 3/2007 |

OTHER PUBLICATIONS

The Handbook of Chemistry & Physics. Publisher Taylor & Francis. $90^{th}$ edition. 2009.*
2008 Ashrae Handbook—Heating, Ventilating, and Air-Conditioning Systems and Equipment (I-P Edition). Chapter 47.1.*
Tapley, Byron. Eshbach's Handbook of Engineering Fundamentals. Fourth edition. Copyright 1990. Chapter 14, p. 22.*
Rules of Thumb for Chemical Engineers—A Manual of Quick, Accurate Solutions to Everyday Process Engineering Problems (Branan, Carl R. 2005 Elsevier, p. 44.*
The Handbook of Chemistry & Physics. Publisher Taylor & Francis. 90th edition. 2009.*
Buchholz et al., *Modern Superabsorbent Polymer Technnology*, Wiley-VCH, 71-103 (1998).
Frank, Ullmann's Encyclopedia of Industrial Chemistry, 6th Edition, vol. 35, pp. 73-93, Wiley-VCH (2003).

* cited by examiner

*Primary Examiner* — David W Wu
*Assistant Examiner* — Elizabeth Eng
(74) *Attorney, Agent, or Firm* — Marshall, Gerstein & Borun LLP

(57) ABSTRACT

A process for producing water-absorbing polymer particles by neutralizing the monomer and cooling it by means of an indirect heat exchanger, wherein the specific cooling performance of the heat exchanger is less than 10 W/m².

13 Claims, 1 Drawing Sheet

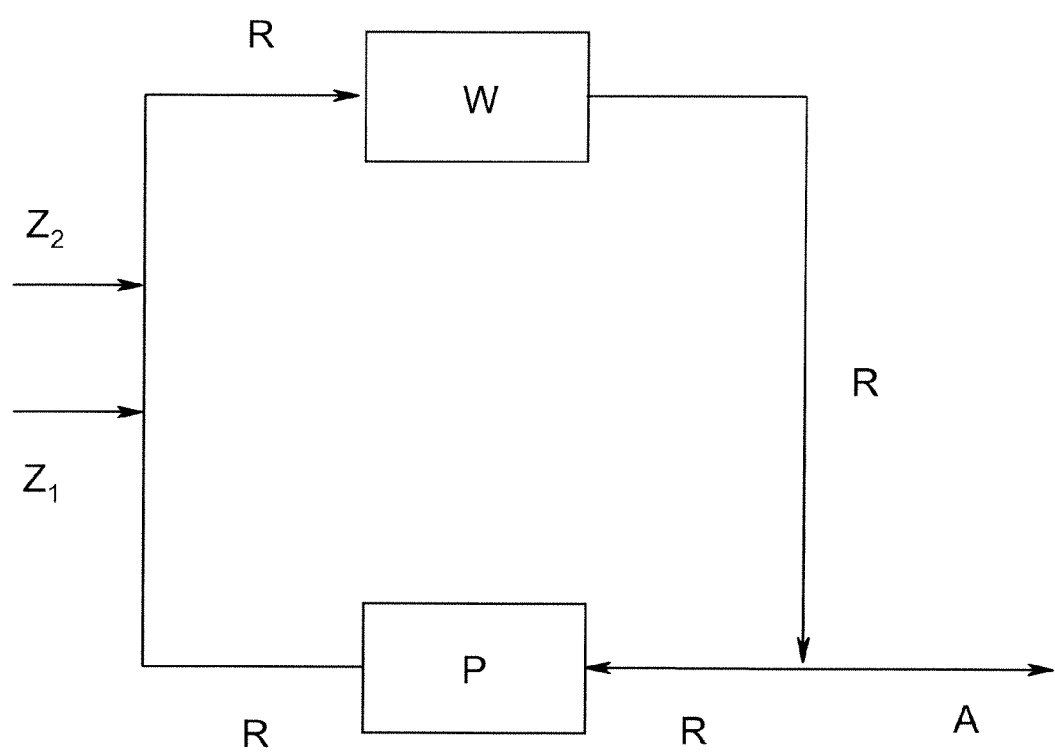

PROCESS FOR PRODUCING WATER-ABSORBING POLYMER PARTICLES

CROSS-REFERENCE TO RELATED APPLICATIONS

This application claims the benefit of U.S. provisional patent application No. 61/079,991, filed Jul. 11, 2008, incorporated by reference herein in its entirety.

The present invention relates to a process for producing water-absorbing polymer particles, wherein the monomer is neutralized and cooled by means of an indirect heat exchanger.

Water-absorbing polymers are used to produce diapers, tampons, sanitary napkins and other hygiene articles, but also as water-retaining agents in market gardening. The water-absorbing polymer particles are also referred to as superabsorbents and consist of hydrophilic polymers which are so highly crosslinked that they are no longer soluble.

The preparation of the water-absorbing polymers is described, for example, in the monograph "Modern Superabsorbent Polymer Technology", F. L. Buchholz and A. T. Graham, Wiley-VCH, 1998, pages 71 to 103, and in Ullmann's Encyclopedia of Industrial Chemistry, 6$^{th}$ edition, volume 35, pages 73 to 93.

Both in continuous and in batchwise polymerization, partially neutralized acrylic acid is typically used as the monomer. Suitable neutralization processes are described, for example, in EP 0 372 706 A2, EP 0 574 260 A1, WO 2003/051415 A1, EP 1 470 905 A1, WO 2007/028751 A1, WO 2007/028746 A1 and WO 2007/028747 A1.

EP 0 372 706 A2 describes a three-stage neutralization process in which, in a first stage, acrylic acid and sodium hydroxide solution are metered in simultaneously, so as to attain a degree of neutralization of from 75 to 100 mol %, and the degree of neutralization is raised in a second stage to from 100.1 to 110 mol % in order to hydrolyze the diacrylic acid present as an impurity in the acrylic acid used, and a degree of neutralization of from 20 to 100 mol % is established in a third stage by addition of further acrylic acid.

EP 0 574 260 A1 discloses, at page 7 lines 38 to 41, that the neutralization advantageously involves initially charging sodium hydroxide solution and then adding acrylic acid with cooling.

WO 2003/051415 A1 teaches a process for preparing water-absorbing polymers, in which the monomer solution has a minimum temperature of 40° C.

EP 1 470 905 A1 describes, in the examples, the continuous neutralization of acrylic acid immediately upstream of the polymerization reactor. Owing to the heat of neutralization, the temperature rises to 95° C.

WO 2007/028751 A1 discloses a process for continuous neutralization, wherein the temperature peaks which occur in the course of neutralization are minimized.

WO 2007/028746 A1 describes a continuously monitored neutralization process.

WO 2007/028747 A1 teaches the use of a preneutralized monomer solution for preparation of monomer solutions with a different degree of neutralization.

A disadvantage in the case of use of warm or hot monomer solutions is their high tendency to polymerize and the associated tendency to form polymer deposits in the plant parts upstream of the actual polymerization reactor. Preference is therefore given to using cold monomer solutions. However, even in the case of use of cold monomer solutions, especially in the case of monomer solutions with a high solids content, undesired salt deposits are found in the plant parts upstream of the actual polymerization reactor after prolonged operation.

It was an object of the present invention to provide an improved process, especially a reliable process in terms of operation, for producing water-absorbing polymer particles.

The object is achieved by a process for producing water-absorbing polymer particles by polymerizing a monomer solution comprising a) at least one ethylenically unsaturated monomer bearing acid groups,
b) at least one crosslinker,
c) at least one initiator,
d) optionally one or more ethylenically unsaturated monomers copolymerizable with the monomers specified under a) and
e) optionally one or more water-soluble polymers, by at least partially neutralizing the monomer a) and removing the heat of neutralization at least partially by means of an indirect heat exchanger by means of a cooling medium, wherein the specific cooling performance of the heat exchanger is less than 10 W/cm$^2$.

The specific cooling performance is the quotient of total cooling performance of the heat exchanger and total heat exchange area of the heat exchanger.

The specific cooling performance of the heat exchanger is preferably less than 5 W/cm$^2$, more preferably less than 2 W/cm$^2$, most preferably less than 1 W/cm$^2$. The temperature of the cooling medium, especially at the inlet of the heat exchanger, is preferably at least 10° C., more preferably at least 15° C., most preferably at least 20° C. The monomer solution is cooled in the heat exchanger preferably to less than 40° C., more preferably to less than 35° C., most preferably to less than 30° C. The heat exchanger is preferably operated in countercurrent.

The present invention is based on the finding that the solubility limit in the heat exchanger can be exceeded partially as a result of cooling, even though this should not yet be the case on the basis of the temperatures measured in the neutralization. This involves crystallization of salt of the neutralized ethylenically unsaturated monomers bearing acid groups. Especially in the case of monomer solutions with a high solids content, these crystals dissolve only very slowly and lead to undesired salt deposits in pipelines and vessels.

The process according to the invention is therefore particularly advantageous at a water content of the monomer solution of preferably at most 70% by weight, more preferably at most 65% by weight, most preferably at most 60% by weight.

The process according to the invention is also particularly advantageous at a degree of neutralization of at least 50 mol %, more preferably at least 60 mol %, most preferably at least 65 mol %.

The degree of neutralization is the molar ratio of neutralized ethylenically unsaturated monomer bearing acid groups after the neutralization to the total amount of ethylenically unsaturated monomer bearing acid groups used before the neutralization multiplied by 100%.

The temperature of the ethylenically unsaturated monomer bearing acid groups supplied to the neutralization is typically from 0 to 40° C., preferably from 5 to 35° C., more preferably from 10 to 30° C., most preferably from 15 to 25° C., ensuring a sufficient distance from the melting point. In the case of use of acrylic acid, the temperature should never be below 15° C.

A preferred base is aqueous alkali. Aqueous alkali includes all alkaline aqueous solutions, i.e. aqueous solutions with a pH of at least 8, preferably at least 10, more preferably at least 12, most preferably at least 14.

The alkaline salts usable in the aqueous neutralizing agent are preferably alkali metal hydroxides, alkali metal oxides, alkali metal carbonates and alkali metal hydrogencarbonates, and mixtures thereof Instead of alkali metal salts, it is also possible to use ammonium salts. Sodium and potassium are particularly preferred as alkali metals, but very particular preference is given to sodium hydroxide, sodium carbonate or sodium hydrogencarbonate and mixtures thereof. Preference is given to using aqueous solutions. Typically, the proportion of the alkaline salt in the aqueous solution is at least 10% by weight, preferably at least 20% by weight, more preferably at least 30% by weight, most preferably at least 40% by weight.

The temperature of the aqueous alkali is typically from 0 to 45° C., preferably from 5 to 40° C., more preferably from 10 to 35° C., most preferably from 15 to 30° C., avoiding oversaturation and hence precipitation.

When the alkali content of the aqueous alkali is at least 25% by weight, higher temperatures are advantageous, typically from 10 to 60° C., preferably from 20 to 55° C., more preferably from 30 to 50° C., most preferably from 40 to 45° C.

The neutralization is preferably performed continuously. This means that ethylenically unsaturated monomer bearing acid groups and/or base is supplied to the neutralization region and neutralized solution is simultaneously withdrawn from the neutralization region. Startup and shutdown operations of the continuous neutralization process are of course excluded from this.

The neutralization region is the region in which the neutralization substantially takes place, i.e. the region in which ethylenically unsaturated monomer bearing acid groups and base react to form salts (neutralization).

The neutralization is substantially complete when the conversion in the neutralization is at least 90%, preferably at least 95%, more preferably at least 98%, most preferably at least 99%.

The distance between neutralization and polymerization is typically at least 1 m, preferably at least 5 m, more preferably at least 10 m, most preferably at least 20 m, and typically not more than 100 m, the distance being that between metered addition of alkali in the neutralization and the polymerization reactor.

In addition, the neutralized solution can be diluted with water. The dilution with water can be used to adjust the solids content of the neutralized solution during or after the neutralization.

The temperature of the water is typically from more than 0 to 40° C., preferably from 5 to 35° C., more preferably from 10 to 30° C., most preferably from 15 to 25° C.

Preference is given to premixing water and base. In this case, the heat of dissolution released can be removed actually before the neutralization, for example by means of suitable heat exchangers.

In a particularly preferred embodiment of the present invention, a portion of the neutralized solution is recycled into the neutralization.

The recycling allows the heat of neutralization and the heat of dissolution to be distributed better and temperature peaks (peak temperature) in the mixture to be minimized. The proportion of recycled neutralized solution is typically from 25 to 99%, preferably from 33 to 98%, more preferably from 50 to 95%, most preferably from 80 to 90%, based in each case on the neutralized solution.

The ethylenically unsaturated monomer bearing acid groups, the base and optionally the water can be metered into the recycled neutralized solution at any desired points. Preference is given to metering in the liquids in succession, more preferably base and ethylenically unsaturated monomer bearing acid groups in succession, or water, base and ethylenically unsaturated monomer bearing acid groups in succession.

Advantageously, at least one of the reactants is metered in via two or more separate addition points.

For example, the reactants can be metered in via two, three, four, five or six addition points, in which case the addition points are preferably arranged such that they have a common axis (for two addition points) or form a symmetrical star (for at least three addition points) and the axis or star is at right angles to the flow direction of the neutralized solution (multiple addition points).

Particularly advantageously, the base is metered in when two, three or four multiple addition points are arranged in succession.

The division into a plurality of addition points brings about more homogeneous mixing and lower temperature peaks, which reduces the risk of undesired polymerization.

In a further embodiment, water and base are metered in such that the water surrounds the base on entry into the neutralization. To this end, it is possible to use, for example, two tubes with one inserted inside the other, the base being metered in through the inner tube and the water through the annular gap between inner and outer tube.

An illustrative inventive neutralization is shown by FIG. 1, where the reference numerals have the following meanings:
$Z_1$ to $Z_2$ inlets for reactants 1 and 2
A outlet
P pump
R ring line
W heat exchanger By means of a pump P, neutralized solution is recycled partially via the ring line R. The remainder of the neutralized solution is sent to further use via the outlet A. Sodium hydroxide solution is preferably metered in via the inlet $Z_1$ and acrylic acid is preferably metered in via the inlet $Z_2$.

In order that the reactants are mixed very intensively into the recycled neutralized solution, the flow at the mixing point should be very turbulent. The mixing point is the site where the particular reactant meets the recycled neutralized solution.

In a preferred embodiment of the present invention, at least one of the reactants is metered into a Venturi tube; preference is given to metering all reactants into a Venturi tube; particular preference is given to metering all reactants into a common Venturi tube.

A Venturi tube is a tube constriction of limited length, in which pressure drop is converted essentially reversibly to kinetic energy. To this end, the cross section $F_1$ is reduced to the cross section $F_2$ over the distance $L_1$, the cross section $F_2$ is kept constant over the distance $L_2$, and then the cross section $F_2$ is widened again to the cross section $F_1$ over the distance $L_3$. The cross section $F_1$ is greater than the cross section $F_2$ and the length $L_3$ is greater than the length $L_1$.

The reactants for the neutralization are preferably metered in in the region of the distance $L_2$ with the cross section $F_2$.

The optimal design of a Venturi tube is known per se to those skilled in the art. The Venturi tube is preferably designed such that the pressure in the region of the distance $L_2$ is less than ambient pressure (suction conveying) and/or that the flow in the region of the distance $L_2$ is turbulent, where the Reynolds number should be at least 1000, preferably at least 2000, more preferably at least 3000, most preferably at least 4000, and typically less than 10,000.

The present invention further provides a process for producing water-absorbing polymers, in which a neutralized solution prepared by the neutralization process according to the invention is used as the monomer solution.

The inventive continuous neutralization process is preferably combined with a continuous polymerization process, preference being given to continuously performing all process steps, such as neutralization, polymerization, drying, grinding, screening, surface postcrosslinking, screening.

The water-absorbing polymer particles are produced by polymerizing a monomer solution and are typically water-insoluble.

The monomers a) are preferably water-soluble, i.e. the solubility in water at 23° C. is typically at least 1 g/100 g of water, preferably at least 5 g/100 g of water, more preferably at least 25 g/00 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene gycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 70% by weight, more preferably from 45 to 65% by weight, most preferably from 50 to 60% by weight. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution is comminuted continuously by, for example, contrarotatory stirrer shafts, as described in WO 2001/38402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 50 to 95 mol %, more preferably from 60 to 80 mol %, most preferably from 65 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably from 0.5 to 15% by weight, more preferably from 1 to 10% by weight, most preferably from 2 to 8% by weight, the residual moisture content being determined by the EDANA (European Disposables and Nonwovens Association) recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight, most preferably from 40 to 60% by weight. Optionally, it is, however, also possible to use a fluidized bed drier or a heated plowshare mixer for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 μm, more preferably from 250 to 600 μm, very particularly from 300 to 500 μm. The mean particle size of the product fraction may be determined by means of the EDANA (European Disposables and Nonwovens Association) recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 μm is preferably at least 90% by weight, more preferably at least 95% by weight, most preferably at least 98% by weight.

Polymer particles with too small a particle size lower the permeability (SFC). The proportion of excessively small polymer particles ("fines") should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles after the surface postcrosslinking.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until in an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably from 0.001 to 2% by weight, more preferably from 0.02 to 1% by weight, most preferably from 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, from 0.001 to 1.5% by weight, preferably from 0.005 to 1% by weight, more preferably from 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers, plowshare mixers and paddle mixers. Particular preference is given to horizontal mixers such as plowshare mixers and paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, Lödige mixers, Bepex mixers, Nauta mixers, Processall mixers and Schugi mixers. However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio is preferably from 20:80 to 40:60.

The thermal drying is preferably carried out in contact driers, more preferably paddle driers, most preferably disk driers. Suitable driers are, for example, Bepex driers and Nara driers. Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range from 100 to 250° C., preferably from 120 to 220° C., more preferably from 130 to 210° C., most preferably from 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or subsequently moistened. Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles produced by the process according to the invention have a moisture content of preferably from 0 to 15% by weight, more preferably from 0.2 to 10% by weight, most preferably from 0.5 to 8% by weight, the water content being determined by the EDANA (European Disposables and Nonwovens Association) recommended test method No. WSP 230.2-05 "Moisture Content".

The water-absorbing polymer particles produced by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by the EDANA (European Disposables and Nonwovens Association) recommended test method No. WSP 241.2-05 "Centrifuge Retention Capacity".

The water-absorbing polymer particles produced by the process according to the invention have an absorption under a pressure of 49.2 g/cm$^2$ of typically at least 15 g/g, preferably at least 20 g/g, preferentially at least 22 g/g, more preferably at least 24 g/g, most preferably at least 26 g/g. The absorption under a pressure of 49.2 g/cm$^2$ of the water-absorbing polymer particles is typically less than 35 g/g. The absorption under a pressure of g/cm$^2$ is determined analogously to the EDANA (European Disposables and Nonwovens Association) recommended test method No. WSP 242.2-05 "Absorption Under Pressure", except that a pressure of 49.2 g/cm$^2$ is established instead of a pressure of 21.0 g/cm$^2$.

EXAMPLE

In a continuous apparatus according to FIG. 1, acrylic acid was neutralized with sodium hydroxide solution.

The diameter of the ring line R was 20 cm, the mass flow in the ring line R upstream of the inlet $Z_1$ was 349 t/h, the temperature of the mass flow in the ring line R upstream of the inlet $Z_1$ was from 25 to 30° C., the acrylic acid mass flow was 11.5 t/h, the 50% by weight sodium hydroxide solution mass flow was 8.4 t/h and the water mass flow was 15 t/h. The temperature of the reactant mass flows was in each case approx. 23° C.

Sodium hydroxide solution and water were premixed. The sodium hydroxide solution/water mixture and acrylic acid were metered into a common Venturi tube. The length of the Venturi tube was 93.2 cm, and the Venturi tube narrowed to a diameter of 10 cm over a distance of 8.4 cm, maintained the diameter of 10 cm over a distance of 27.6 cm and widened again to a diameter of 20 cm over a distance d of 57 cm. In each case two inlets $Z_1$ and $Z_2$ opened into the Venturi tube. The distance of the two inlets $Z_1$ from the point where the Venturi tube narrows to 10 cm was 5 cm, the distance between the two inlets $Z_2$ from the two inlets $Z_1$ was 8 cm, and the diameter of the two inlets $Z_1$ and $Z_2$ in each case was 3.5 cm. The two inlets $Z_1$ and $Z_2$ in each case are arranged opposite one another, the axis connecting the two inlets $Z_1$ being rotated by 90° relative to the axis connecting the two inlets $Z_2$.

The heat exchanger W was a tube bundle heat exchanger with an effective exchange area of 310 m$^2$ and a cooling performance of 2000 kW, corresponding to a specific cooling performance of 0.645 W/cm$^2$. The mass flow of the ring line R was cooled in the heat exchanger W from 35 to 40° C. to from 25 to 30° C. The coolant inlet temperature was from 25 to 29° C. The heat exchanger was operated in countercurrent.

The partially neutralized monomer solution prepared had a degree of neutralization of 65.6 mol % and a solids content of 39.6% by weight. The ring line R and the discharge line A were free of deposits even after prolonged operation.

100 g of the monomer solution prepared were cooled. At a temperature of −7° C., sodium acrylate separated out on the vessel wall.

The example shows that the tube bundle heat exchanger could be operated without disruption by the process according to the invention. When, in contrast, the monomer solution is cooled further, i.e. the specific cooling performance of the tube bundle heat exchanger is increased, salt deposits are found in the tube bundle heat exchanger, even though the temperature of the cooled monomer solution is still significantly above −7° C.

What is claimed:

1. A process for producing water-absorbing polymer particles by polymerizing a monomer solution comprising
   a) at least one ethylenically unsaturated monomer bearing acid groups,
   b) at least one crosslinker,
   c) at least one initiator,
   d) optionally one or more ethylenically unsaturated monomer copolymerizable with the monomer a) and
   e) optionally one or more water-soluble polymer, by at least partially neutralizing the monomer a) and removing a heat of neutralization at least partially using an indirect heat exchanger using a cooling medium, wherein a specific cooling performance of the heat exchanger is less than 10 W/cm$^2$.

2. The process according to claim 1, wherein a temperature of the cooling medium in the heat exchanger is at least 10° C.

3. The process according to claim 1, wherein the monomer solution is cooled to less than 40° C. in the heat exchanger.

4. The process according to claim 1, wherein the heat exchanger is operated in countercurrent.

5. The process according to claim 1, wherein a water content of the monomer solution is at most 70% by weight.

6. The process according to claim 1, wherein a degree of neutralization of the neutralized monomer a) is at least 50 mol %.

7. The process according to claim 1, wherein the monomer a) is acrylic acid.

8. The process according to claim 1, wherein the neutralized monomer a) is recycled at least partially into the neutralization.

9. The process according to claim 8, wherein between 25 and 95% of the neutralized monomer a) is recycled.

10. The process according to claim 1, wherein the water-absorbing polymer particles have a centrifuge retention capacity of at least 15 g/g.

11. The process of claim 1 wherein the specific cooling performance of the heat exchanger is less than 5 W/cm$^2$.

12. The process of claim 1 wherein the specific cooling performance of the heat exchanger is less than 2 W/cm$^2$.

13. The process of claim 1 wherein the specific cooling performance of the heat exchanger is less than 1 W/cm$^2$.

* * * * *